United States Patent [19]

Speer et al.

[11] Patent Number: 4,594,418

[45] Date of Patent: Jun. 10, 1986

[54] ANTITUMOR PLATINUM COMPLEXES

[75] Inventors: Robert J. Speer, Richardson; David P. Stewart, Fort Worth, both of Tex.

[73] Assignee: Bristol-Myers Company, New York, N.Y.

[21] Appl. No.: 781,629

[22] Filed: Sep. 30, 1985

Related U.S. Application Data

[62] Division of Ser. No. 592,987, Mar. 23, 1984, Pat. No. 4,562,275.

[51] Int. Cl.[4] ............................................. C07F 15/00
[52] U.S. Cl. ....................................... 544/225; 556/7; 556/19; 556/24; 556/26; 556/137
[58] Field of Search ............... 556/7, 19, 24, 26, 137; 544/225

[56] References Cited

U.S. PATENT DOCUMENTS

| | | | |
|---|---|---|---|
| 4,115,418 | 9/1978 | Gale et al. | |
| 4,169,846 | 10/1979 | Kidani et al. | |
| 4,255,347 | 3/1981 | Kidani et al. | 556/137 |
| 4,256,652 | 3/1981 | Kidani et al. | |
| 4,284,579 | 8/1981 | Meischen et al. | |
| 4,359,425 | 11/1982 | Totani et al. | |
| 4,410,544 | 10/1983 | Berg et al. | 556/137 |
| 4,466,924 | 8/1984 | Verleek et al. | 556/137 |

FOREIGN PATENT DOCUMENTS

| | | |
|---|---|---|
| 0055300 | 7/1982 | European Pat. Off. |
| 2003468 | 3/1979 | United Kingdom |
| 2024823 | 1/1980 | United Kingdom |
| 2093845 | 9/1982 | United Kingdom |

OTHER PUBLICATIONS

Chemical Abstracts 92 33788r (1980).
Chemical Abstracts 92 220697x (1980).
J. Clin. Oncol. 8(2):44–50 (1978), Speer et al.
J. Inorg. Biochem. 11:139–149 (1979), Hall et al.
Gann 67:921–922 (1976).
Bioinorg. Chem. 2:187–210 (1973), Cleare et al.
Cancer Treat. Rep. 61(8):1519–1525 (1977), Schwartz et al.
J. Med. Chem. 21(12):1315–1318 (1978), Kidani et al.
J. Clin. Hematol. Oncol. 7(4):867–876 (1977), Stewart et al.
J. Clin. Hematol. Oncol. 7(1):231–241 (1977), Hall et al.
J. Clin. Hematol. Oncol. 7(1):220–230 (1977), Ridgway et al.

*Primary Examiner*—Helen M. S. Sneed
*Attorney, Agent, or Firm*—David M. Morse

[57] ABSTRACT

Novel platinum(II) complexes of 1,2-diaminocyclohexane, 1-aminomethylcyclooctylamine and 1,2-diamino-2,4-dimethylpentane are provided. Such complexes are of use in inhibiting the growth of certain mammalian tumors.

6 Claims, No Drawings

ANTITUMOR PLATINUM COMPLEXES

CROSS-REFERENCE TO RELATED APPLICATION

This application is a division of our application Ser. No. 592,987 filed Mar. 23, 1984, now U.S. Pat. No. 4,562,275.

BACKGROUND OF THE INVENTION

1. Field of the Invention

This invention relates to novel platinum(II) complexes having antitumor activity. More particularly, it relates to novel antitumor platinum(II) complexes of 1,2-diaminocyclohexane, 1-aminomethylcyclooctylamine and 1,2-diamino-2,4-dimethylpentane.

2. Description of the Prior Art

Various platinum(II) complexes of 1,2-diaminocyclohexane, 1-aminomethylcyclooctylamine and 1,2-diamino-2,4-dimethylpentane have been disclosed in the scientific and patent literature as having antitumor activity.

With respect to platinum(II) complexes of 1,2-diaminocyclohexane, the original antitumor complex appears to have been dichloro(1,2-diaminocyclohexane)platinum(II) reported, for example, in *Bioinorg. Chem.* 2: 187–210 (1973). The chloride ligands in this complex were then replaced by various inorganic and organic ligands such as nitrato, methanesulfonato, tartrato, sulfato, methylmalonato, orthophosphato, acetylacetonato, pyruvato, phthalato, oxalato, glycerophosphato, gluconato, glycerato, etc. (see, for example, *Cancer Treat. Rep.* 61(8): 1519–1525 (1977). These and other analogs are disclosed in U.S. Pat. No. 4,169,846, *J. Med. Chem.* 21(12): 1315–1318 (1978), *J. Clin. Hematol. Oncol.* 7(4): 867–876 (1977)-see bis(monobromoacetato) analog, *J. Clin. Hematol. Oncol.* 7(1): 231–241 (1977); U.K. Patent application No. 2,003,468A-see 4 carboxyphthalato analog, *J. Clin. Hematol. Oncol.* 7(1): 220–230 (1977)-see analogs of ligands such as ketomalonate, 1,2-dibromomaleate, 1,2-dibromosuccinate, *J. Clin. Hematol. Oncol.* 8(2): 44–50 (1978)-note disclosure of analog of the formula

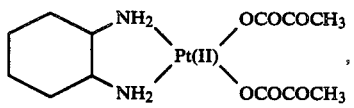

U.S. Pat. No. 4,115,418, U.S. Pat. No. 4,256,652 and U.S. Pat. No. 4,284,579-note preparation of cis-dihydroxy(1,2-diaminocyclohexane)platinum(II) and analog with N-phosphonoacetyl-L-aspartato ligand.

*J. Inorg. Biochem.* 11: 139–149 (1979) discloses preparation of 1-aminomethylcyclooctylamine and 1,2-diamino-2,4-dimethylpentane (starting material for certain complexes of the present invention) as well as complexes of such amine ligands with ligands such as $Cl^-$, $SO_4^=$, $CH_3(COO^-)_2$ and $(BrCH_2COO^-)_2$.

U.S. Pat. No. 4,359,425 discloses antitumor organoplatinum complexes of the general formula

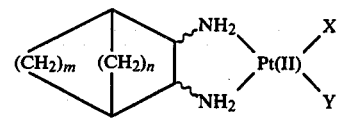

wherein X and Y each or taken together represent a mono- or bi-functional ligand selected from the group consisting of halogenato, nitrato, sulfonato, monocarboxylato, sulfato and dicarboxylato and each of n and m is an integer of 1 or 2.

European Patent Application No. 55,300 discloses as antitumor agents platinum(II) complexes of the formula

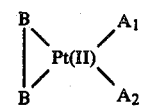

wherein —B—B— represents

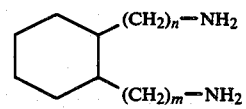

or

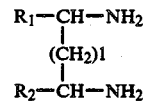

in which $R_1$ and $R_2$ are the same or different and each is hydrogen, an alkyl group or an aryl group, and n, m and l are 0 or an integer of from 1 to 3, at least one of $A_1$ and $A_2$ is

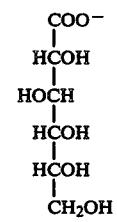

(hereinafter referred to as a ligand of D-gluconic acid)

and the other is the ligand of D-gluconic acid, $Cl^-$, $Br^-$, $I^-$, $F^-$, $XCH_2COO^-$ (in which X is a halogen atom), $NO_3^-$, $SO_4^{-2}$, $H_2PO_4^-$ or $H_2O$ or, when taken together, $A_1$ and $A_2$ may form a ring together with Pt(II), in the latter case —$A_1$—$A_2$— being the ligand of D-gluconic acid.

U.K. Patent Application No. 2,093,845 discloses as antitumor agents platinum(II) complexes of the formula

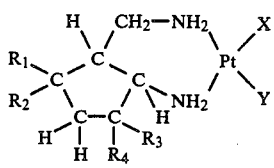

wherein either $R_1$ and $R_2$ independently are hydrogen or a substituted or unsubstituted alkyl, cycloalkyl, aryl or aralkyl group or $R_1$ and $R_2$ when taken together may be a substituted or unsubstituted cycloalkyl group, $R_3$ and $R_4$ are each independently hydrogen or a substituted or unsubstituted alkyl, aryl or aralkyl group and X is a chlorine, bromine or iodine atom, a sulfate radical, a substituted or unsubstituted carboxylate radical and Y independently from X is a chlorine, bromine or iodine atom, a hydroxyl group, a nitrate group or a carboxylate group.

U.K. Patent Application No. 2,024,823A discloses as antitumor agents platinum(II) complexes of the formula

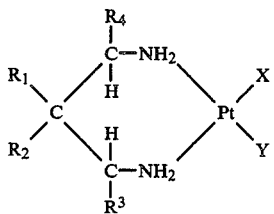

in which $R_1$ and $R_2$ are each independently a hydrogen atom or an optionally substituted alkyl, cycloalkyl, aryl or aralkyl group, or $R_1$ and $R_2$ together are an optionally substituted cycloalkyl group, $R_3$ and $R_4$ are each independently a hydrogen atom or an optionally substituted alkyl, aryl or aralkyl group, and X is an anionic group.

The amine ligand 1,2-diaminocyclohexane may be used as a mixture of cis-, trans-d-and trans-l-isomers to produce the corresponding isomer mixture derived from such starting material. Alternatively and preferably, the 1,2-diaminocyclohexane may be separated into the individual cis-, trans-d- and trans-l-isomers by the procedure described, for example, in U.S. Pat. No. 4,169,846. While all of these individual isomers may be utilized to prepare the complexes of the present invention, the preferred starting material is the trans-l-isomer, hereinafter referred to below as the trans(−)-isomer. This isomer has previously been reported to confer the highest activity in other 1,2-diaminocyclohexane platinum(II) complexes (see, for example, Gann 67: 921–922, 1976 and J. Clin. Hematol. Oncol. 8(2): 44–50, 1978).

While a large number of platinum(II) complexes have been disclosed as having some antitumor activity, there remains a need for new platinum(II) complexes which will have more advantageous properties, i.e. greater activity, broader spectrum, less toxicity, etc. Especially desirable are platinum complexes having significant advantages over cisplatin, the only platinum complex presently being marketed as an anticancer agent.

SUMMARY OF THE INVENTION

The present invention provides in one aspect novel platinum(II) complexes of the formula

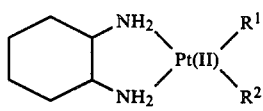

wherein the stereoisomerism of 1,2-diaminocyclohexane is cis-, trans(+)- or trans(−)- and $R^1$ and $R^2$ are both

or $R^1$ and $R^2$ when taken together represent a group of the formula

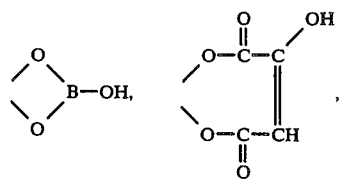

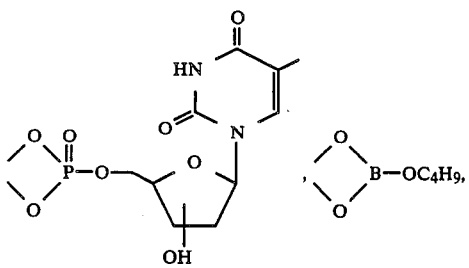

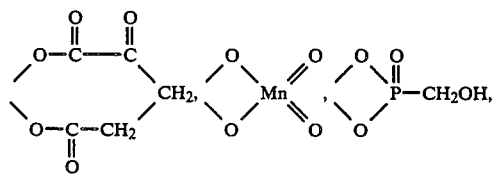

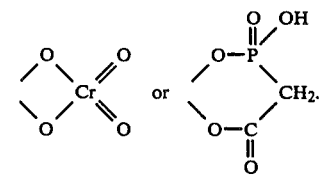

In another aspect the present invention provides the platinum(II) complex of the formula

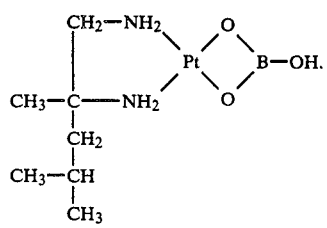

In yet another aspect the present invention provides the platinum(II) complexes of the formula

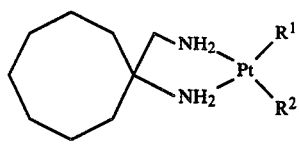

wherein $R^1$ and $R^2$ when taken together represent

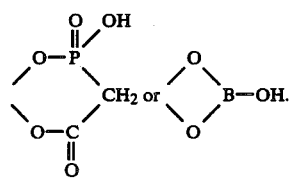

The complexes provided according to the present invention demonstrate high antitumor activity when tested against experimental mouse tumors.

DETAILED DESCRIPTION OF THE INVENTION

The complexes of the present invention are prepared from the corresponding dichloro platinum(II) complexes which have been descibed in the literature. Synthesis of the dichloro complexes of 1-aminomethylcyclooctylamine and 1,2-diamino-2,4-dimethylpentane is disclosed, for example, in *J. Inorg. Biochem.* 11: 139–149 (1979) while synthesis of cis-, trans(+)- and trans(−)-dichloro(1,2-diaminocyclohexane)platinum(II) is described, for example, in U.S. Pat. No. 4,169,846. As mentioned above, while any of the cis-, trans(+)- or trans(−)-isomers of the dichloro(1,2-diaminocyclohexane)platinum(II), or the mixture of isomers, can be used as the starting material to prepare the novel complexes of 1,2-diaminocyclochexane disclosed herein, it is preferred to use the trans(−)-starting material since the biological activity of the end-products is somewhat higher using this material.

Synthesis of the complexes of the present invention using the dichloro platinum(II) complexes is carried out by conventional procedures used to make other platinum(II) complexes known in the art.

In one suitable procedure, for example, the appropriate dichloro complex is reacted with the silver salt of the desired ligand. Typically about 1 mmol of the dichloro complex is reacted with about 0.95 mmol of the appropriate disilver salt in water. AgCl precipitates from solution and is filtered off. The desired complex is then isolated from the filtrate as by evaporation at low temperature in vacuo. The product, if desired, may be washed with an appropriate organic solvent (in which it is substantially insoluble) prior to drying in vacuo. This procedure is used, for example, in Examples 6, 8 and 9 below.

Another suitable procedure involves first forming in situ the dinitrato platinum(II) complex and then reacting this intermediate with an alkali metal salt of the desired ligand. Typically about 1 mmol of the dichloro complex is reacted with about 1.95 mmol $AgNO_3$ in water in the dark at 20°–70° C. for 1–3 hours. The reaction mixture is then generally stirred at room temperature for about 24 hours, chilled (e.g. to about 4° C.) and filtered. To the filtrate is added an aqueous solution of about 1 mmol (in the case of a bidentate ligand) or 2 mmol (in the case of a monodentate ligand) of the desired ligand. If sufficiently insoluble in water, the desired complex generally precipitates on heating to about 70°–80° C. and gradual cooling to 4° C. The precipitated complex can then be recovered by filtration. This procedure is appropriate if the desired complex is of low aqueous solubility and is illustrated in Example 3 below.

An especially preferred procedure involves conversion of the dichloro starting material to the dihydroxy complex and then reaction of this intermediate with the desired ligand. Typically an aqueous solution of the dichloro complex is reacted with $Ag_2SO_4$ and stirred in the dark at room temperature for about 24 hours. The resulting solution is filtered. The absence of silver ions in the filtrate indicates the reaction is complete and that the sulfato complex has been formed in solution. There is then added to the filtrate $Ba(OH)_2$ and the solution is stirred in the dark for another 24 hours. The solution is then filtered to remove $BaSO_4$. At this point the aqueous filtrate containing the dihydroxy platinum(II) intermediate in solution is then reacted with the desired ligand to give the corresponding end-product which can be isolated from aqueous solution, for example by evaporation. This procedure is illustrated in Examples 1–2, 4–5, 7 and 10–14 below.

Product complexes obtained according to the present invention generally require no further purification. However, if desired, the complexes may be purified by conventional procedures, for example by dissolving in a suitable solvent (e.g. water, dimethylformamide, ethanol, etc.), and precipitating from solution by addition of a large excess of a solvent in which the desired complex is only slightly soluble (e.g. ethanol, acetone, diethyl ether, etc.). Products can then be dried over anhydrous silica gel in vacuo in the dark.

Complexes may be tested for identity and homogeneity by IR spectroscopy and thin layer chromatography using the TLC systems described by Hall, et al. in *J. Inorg. Biochem.* 11: 139–149 (1979).

BIOLOGICAL PROPERTIES OF COMPLEXES

The antitumor activities of the complexes provided by the present invention have been determined against L-1210 leukemia in the mouse and, for certain of the complexes, against other mouse tumor systems.

Results of antitumor testing against the transplantable mouse tumors L1210 leukemia, cisplatin-resistant L1210 leukemia, B16 melanoma, Madison 109 lung carcinoma and colon 26 carcinoma are shown below in Tables 1 and 2.

In Table 1 are shown the maximum % T/C values obtained for each platinum compounds versus L1210 leukemia using both single and qd 1→5 dosing. Also shown in Table 1 are testing results against a cisplatin resistant line of L1210 leukemia.

Table 2 shows the maximum % T/C values obtained for each of the selected compounds against ip B16 melanoma, C26 carcinoma and M109 tumors. Also shown are the concomitant maximum effects obtained for cisplatin. A ratio of each compounds maximum effect relative to that of cisplatin is also included.

TABLE 1

Antitumor Activity vs. L1210 Leukemia
Max % T/C* - Cures/total (O.D., mg/kg/inj)

| Compound (Example No) | L1210 Day 1 | L1210 QD 1→5 | L1210/CDDP** Day 1 |
|---|---|---|---|
| 1 | (a)214(16) (b)242(8) | 243(2) | 188-2/6(8) |
| 2 | (a)214(30) (b)217(40) | 243(7.5) | 194-4/6(24) |
| 3 | (a)157(48) (a)214(24)+ (b)200(18)+ | 186-2/6(3) | 195(12)+ |
| 4 | (a)200(20) (b)207(18) | 214-1/6(5) | 163(12) |
| 5 | (a)186(10) (b)200(9) | 193(2.5) | 144-2/6(9) |
| 6 | (a)200(40) (b)207(45) | 221(10) | 175(20) |
| 7 | (a)179(3) (b)236(6)+ (c)217(6)+ | (a)Toxic (b)186(1) | 427-5/6(8)+ |
| 8 | (a)214(20) (b)186(18) | 293(2.5) | 181(8) |
| 9 | (a)150(24) (b)200(48) | (a)143(6) (b)214(12) | |
| 10 | (a)171(20) (b)225(24) | 236(10) | 307-5/6(24) |
| 11 | (a)179(20) (b)225(24) | 207(10) | 240-2/6(24) |
| 12 | (a)221(24) (b)275(21) | 293(3) | 340-2/6(14) |
| 13 | (a)229(16) (b)207(16) | 207(4) | 256-2/6(8) |
| 14 | (a)214(16) (b)193(16) | 250(16) | 169-2/6(12) |
| 15 | 236(80) | 193(10) | |

*dying mice only (cures shown separately)
+in intralipid plus ethanol
**CDDP = cisplatin

TABLE 2

Antitumor Activity vs B16 Melanoma, C26 Carcinoma and M109 Carcinoma

Max. % T/C$^a$ - cures/total (O.D.) for Complex/cDDP:Ratio

| Cmpd. Ex. No. | B16 (3x;9x) T/C | Ratio | C26(2x;4x) T/C | Ratio | M109(2x;4x) T/C | Ratio |
|---|---|---|---|---|---|---|
| 1 | 150(1)/186(1.6) | .81 | 134(5)/163(3) | .82 | 147(2)/175(6) | .84 |
| 2 | 150(2)/186(1.6) | .81 | 143(10)/163(3) | .88 | 156(12)/175(6) | .89 |
| 3 | 182(1)/172(0.8) | 1.06 | 119(16)/176-2/8(4) | .68 | 118(12)/153(6) | .77 |
|   | 164(4)/152(6)$^b$ | 1.08 | | | 103(8)/153(6) | .67 |
| 4 | 150(1)/186(1.6) | .81 | 120(5)/163(3) | .74 | 119(8)/175(6) | .68 |
| 5 | 163(4)/191(1.6) | .85 | Not Done | — | 131(6)/155(4) | .85 |
| 6 | 177(6)/191(1.6) | .93 | 109(36)/144(2.5) | .76 | 95(12)/155(4) | .61 |
| 7 | 120(1.2)/220(6) | .55 | Not Done | — | Not Done | — |
| 8 | 160(2)/220(6) | .73 | Not Done | — | Not Done | — |
| 9 | 172(6)/185(1) | .93 | 106(24)/144(2.5) | .74 | 119(20)/163(6) | .73 |
| 10 | 174(9)/212(0.8) | .82 | 100(8)/144(2.5) | .69 | 74(5)/155(4) | .48 |
| 11 | 206(9)/212(0.8) | .97 | 116(8)/144(2.5) | .81 | 114(10)/155(4) | .74 |
| 12 | 229(4)/212(0.8) | 1.08 | 124(24)/144(2.5) | .87 | 135(18)/142(2) | .95 |
| 13 | 167(2)/185(1) | .90 | 88(8)/144(2.5) | .61 | 81(3)/155(4) | .52 |
| 14 | 135(3)/220(6) | .61 | Not Done | — | Not Done | — |
| 15 | 147(3)/189(4) | .77 | Not Done | — | Not Done | — |

$^a$% T/C shown for dying mice only with any cures shown separately
$^b$Sc tumor implant with iv drug dosing.

The results to date from side-effects (toxicity) testing of compounds of the present invention are summarized in Table 3 with more detailed data shown in Tables 4 and 5. LD$_{50}$ values (single dose ip) were determined in BDF$_1$ mice for certain complexes, i.e. those of Examples 5, 7, 8, 10, 12 and 15. The other compounds were in such short supply that they were tested for effects on BUN values using the optimum dose (O.D.) from the L1210 test for dose selection. Results of emesis testing are shown in Table 5 for four compounds.

TABLE 3

Summary - Platinum Complex Side Effects

| Compound (Example No.) | OD (mg/kg/ip) | LD$_{50}$ (mg/kg/ip) | Solubility (mg/ml) | Mouse BUN ↑$^a$ | Emetic in Ferrets (mg/kg/iv) |
|---|---|---|---|---|---|
| Cisplatin | 8 | 14 | 1 | + | + (8) |
| 1 | 16 | ND | 2 | 0 | = (12) |
| 2 | 30 | ND | 3 | 0 | = (16) |
| 3 | 24 | ND | | 0 | |
| 4 | 20 | ND | 2 | 0 | |
| 5 | 10 | 30 | 1.6 | 0 | |
| 6 | 40 | ND | | 0 | = (32) |
| 7 | 3.6 | 11.3 | 1 | 0 | |
| 8 | 20 | 31 | 3 | 0 | = (16) |
| 9 | 48 | ND | | 0 | |
| 10 | 10–20 | 30 | 2 | < | |
| 11 | 20 | ND | | | |
| 12 | 24 | 79 | 3 | 0 | |
| 13 | 16 | ND | | 0 | |
| 15 | 80 | 137 | 7 | < | |

$^a$Effect relative to cisplatin

TABLE 4

Summary: Effects of Platinum Complexes on BUN in BFD$_1$ Mice

| Compound (Example No) | Dose (mg/kg/ip) | Incidence of BUN > 30 mg % | Deaths D.14 | Test No. |
|---|---|---|---|---|
| Cisplatin | 14 (LD$_{50}$) | 70–100% | 50–100% | * |
| | 12 | 60–100% | 20–100% | |
| | 10.5 | 50–100% | 0–50% | |
| | 8 (OD) | 20–100% | 0–40% | |
| 1 | 24 | 0/3 | 3/5 | 1788 |
| | 16 (OD) | 0/5 | 0/5 | |
| 2 | 45 | 0/4 | 1/5 | 1788 |

TABLE 4-continued

Summary: Effects of Platinum Complexes on BUN in BFD₁ Mice

| Compound (Example No) | Dose (mg/kg/ip) | Incidence of BUN > 30 mg % | Deaths D.14 | Test No. |
|---|---|---|---|---|
|  | 30 (OD) | 0/5 | 0/5 |  |
| 3 | 36 | 0/2 | 3/5 | 1788 |
|  | 24 (OD) | 0/3 | 2/5 |  |
| 4 | 30 | 0/5 | 0/5 | 1788 |
|  | 20 (OD) | 0/5 | 0/5 |  |
| 5 | 30 ($LD_{50}$) | 1/9 | 3/10 | 1949 |
|  | 22.5 | 0/10 | 1/10 |  |
|  | 17 | 0/10 | 1/10 |  |
| 6 | 60 | 0/5 | 0/5 | 1925 |
|  | 40 (OD) | 0/5 | 0/5 |  |
| 7 | 11.3 ($LD_{50}$) | 0/10 | 0/10 | 1954 |
|  | 8.5 | 0/10 | 0/10 |  |
|  | 6.4 | 0/10 | 0/10 |  |
| 8 | 31 ($LD_{50}$) | 0/8 | 2/10 | 1940 |
|  | 23 | 0/7 | 3/10 |  |
|  | 17 | 0/9 | 1/10 |  |
| 9 | 72 | 0/5 | 0/5 | 2013 |
|  | 48 (OD) | 0/5 | 0/5 |  |
| 10 | 30 ($LD_{50}$) | 7/10 | 1/10 | 1967 |
|  | 22.5 | 1/10 | 0/10 |  |
|  | 17 | 0/10 | 0/10 |  |
| 11 | 30 | 0/5 | 0/5 | 1925 |
|  | 20 ($LD_{50}$) | 0/5 | 0/5 |  |
| 12 | 79 ($LD_{50}$) | — | 10/10 | 1968 |
|  | 59 | 0/4 | 9/10 |  |
|  | 44 | 1/6 (7) | 6/10 |  |
| 13 | 24 | 0/5 | 0/5 | 1925 |
|  | 16 | 0/5 | 0/5 |  |
| 15 | 137 ($LD_{50}$) | 7/10 | 9/10 | 2014 |
|  | 103 | 2/10 | 3/10 |  |
|  | 77 | 0/10 | 0/10 |  |

*Historical ranges

TABLE 5

Emetic Effects of Platinum Complexes in the Ferret

| Compound (Example No) | Dose (mg/kg) iv | No. With Emesis / No. tested | Episodes | Emesis onset in responding animals (min) |
|---|---|---|---|---|
| 1 | 12* | 1/1 | 14 | 10 |
| 2 | 16 | 1/1 | 3 | 41 |
| 6 | 32* | 2/2 | 13.5 | 17.5 |
| 8 | 16* | 1/1 | 15 | 16 |

*Lethal dose
Compound of Example 8-acute lethality 44 min.

The methods used to evaluate the platinum complexes for antitumor activity and toxicity in animals are summarized below. These methods have been published elsewhere in more detail (Rose, et al, *Cancer Treat. Rep.* 66: 135, 1982; Flurczyk, et al. *Cancer Treat. Rep.* 66: 187, 1982).

Animals

Male and female BDF₁, CDF₁, DBA/2, BALB/c and C57BL/6 mice (17-21 gm) were used for the antitumor evaluations. The toxicity studies were done in male BDF₁ mice (25-29 gm) and castrated male Fitch ferrets (1-1.5 kg).

Tumors

The parent line of L1210 leukemia (L1210) was maintained in DBA/2 mice by ip transplantation of $10^5$ cells at weekly intervals. A subline of L1210 resistant to cisplatin (L1210/CDDP) was maintained in the same manner but the passage mice were treated ip with cisplatin, 4 mg/kg, on Day 4 post-implant. B16 melanoma (B16) was maintained by sc transplant in C57BL/6 mice every two weeks. Madison 109 lung carcinoma (M109) and colon 26 carcinoma (C26) were maintained by sc transplant in BALB/c mice every two weeks.

Antitumor Testing

The level and route of tumor inoculum, host, group size, and drug treatment schedule and route for each tumor type are summarized below in Table 6. Each complex was evaluated initially against L1210 at 4 dose levels per schedule selected on the basis of lethality data provided by the Wadley Institute. In subsequent experiments with the other tumors the complexes were evaluated at a minimum of 3 dose levels selected on the basis of maximum tolerated levels in the L1210 experiments. Cisplatin-treated groups and a saline-treated (or untreated) tumor control group were included in each experiment.

The L1210 experiments were terminated on Day 30 whereas the B16, C26 and M109 experiments were terminated on Day 60 (some C26 experiments were terminated on Day 75). Mice alive at the termination day were autopsied and considered cured if no tumor was visible. Mice were observed daily and comparative antitumor activity relative to cisplatin was determined based on the fraction of mice cured and % T/C, defined as:

$$\frac{\text{Median survival time of treated mice}}{\text{Median survival time of treated mice}} \times 100$$

A complex was considered active if it produced a % T/C value $\geq 125$.

TABLE 6

Summary of Experimental Designs

| Tumor | Level and Route of Inoculum | Mouse Host | Group Size | Drug Treatment Schedule and Route |
|---|---|---|---|---|
| L1210 | $10^6$, ip | CDF₁ | 6 | d.1 or qd 1-5, ip |
| B16 | 0.5 ml 10% brei, ip | BDF₁ | 10 | $q4d^a \times 3$ or qd 1-9, ip |
| C26 | 0.5 ml 1% brei, ip | CDF₁ | 8 | $q3d^b \times 2$ or qd 1-4, ip |
| M109 | 0.5 ml 2% brei, ip | CDF₁ | 8 | $q3d^a \times 2$ or qd 1-4, ip |

[a]Beginning d.1 after tumor implant.
[b]Beginning d.1 or d.5 after tumor implant.

Toxicity Testing

Single-dose ip $LD_{50}$ values were determined in BDF₁ mice for the indicated complexes. The mice, 5-10/dose, were observed for 30 days after dosing and the $LD_{50}$ value calculated by the Weil method (*Biometrics* 8: 249, 1952).

The complexes that were active against L1210 were evaluated for nephrotoxicity by determining their effects on blood urea nitrogen (BUN) levels in mice. Groups of 40-50 mice/experiment were bled from the retro-orbital plexus and individual BUN values determined by a modified urease method using a Centrifichem System 400. The test complex, or saline for controls, was given at several dose levels (5-10 mice/dose) in single ip injections. The highest dose of the complex usually corresponded to its $LD_{50}$ value or 1.5 times its optimal single dose in the L1210 experiment. At least two lower doses were included to evaluate dose-related effects. The BUN values were measured 4 and 7 days after dosing. BUN values $\geq 30$ mg% were considered indicative of drug-induced nephrotoxicity.

Selected complexes were evaluated for emetic effects in ferrets. The test drug was administered iv as a bolus and the animals observed for 6 hours. The time to the first emetic episode (retching and expulsion of vomitus) and the number of episodes were recorded. The initial test dose of each complex was selected base on its potency, relative to cisplatin, to cause lethality in mice. Subsequent test doses were selected based on the emetic response and lethality of the initial dose.

As illustrated by the data shown above, the platinum compounds of the present invention exhibit inhibitory activity against malignant tumors in mammals.

According to one aspect of the invention, therefore, a method is provided for therapeutically treating a mammalian host affected by a malignant tumor which comprises administering to said host an effective tumor-inhibiting dose of a compound of the present invention, i.e. the products described in Examples 1–15 below.

According to another aspect, a pharmaceutical composition is provided which comprises a tumor-inhibiting amount of a compound of the present invention in combination with a pharmaceutically acceptable carrier or diluent.

The platinum compounds of the present invention are preferably administered parenterally in the same manner as other antitumor platinum complexes known in the art, e.g. cisplatin.

Preparations for parenteral administration include sterile aqueous or non-aqueous solutions, suspensions or emulsions. They may also be manufactured in the form of sterile solid compositions which can be dissolved in sterile water, physiological saline or some other sterile injectable medium prior to administration.

It will be appreciated that the actual preferred dosage amounts used will vary according to the particular comound being used, the particular composition formulated, the mode of application and the particular situs, host and disease being treated. In general the compounds are injected intraperitoneally, intravenously, subcutaneously or locally. Many factors that modify the action of the drug will be taken into account by those skilled in the art, for example, age, body weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by those skilled in the art using conventional dosage determination tests.

Illustrative methods for preparing the compounds of the present invention are provided below. These examples, however, are not meant to limit the scope of the invention to the specific procedures employed. Volume ratios used to describe solvent systems are volume/volume.

EXAMPLE 1

Preparation of borato trans(−)-1,2-diaminocyclohexane platinum(II)

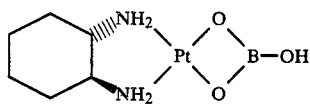

A mixture of cis-dihydroxy-1,2-diaminocyclohexane platinum(II) (686 mg) and boric acid (120 mg) was heated for 1 hour at 50° C. There was a slight color change from yellow to gold. Upon evaporation of the solution to dryness, there was obtained the title product as a gold solid. The product was both water- and alcohol-soluble. The IR was consistent for the indicated structure. When tested in the TLC system isopropanol: ammonium hydroxide (0.1N) (1:1), the product gave an $R_f$ of 0.88 while in a n-butanol:glacial acetic acid:H$_2$O (12:3:5) system, the $R_f$ was 0.52.

EXAMPLE 2

Preparation of oxaloacetato trans(−)-1,2-diaminocyclohexane platinum(II)

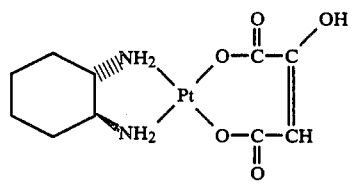

A mixture of cis-dihydroxy-1,2-diaminocyclohexane platinum(II) (343 mg) and oxaloacetic acid (140 mg) was heated for two hours at 50° C. The solution changed from yellow to gold. Upon evaporation of the solution to dryness, there was obtained the title product as a gold solid. The product was both water- and alcohol-soluble and gave the following $R_f$ values in the indicated TLC systems:

| | |
|---|---|
| n-butanol:glacial acetic acid:H$_2$O (12:3:5) | 0.64 |
| isopropanol: 0.1N NH$_4$OH (1:1) | 0.90 |

The IR was consistent for the indicated structure.

EXAMPLE 3

Preparation of bis-heptafluorobutyrato trans(−)-1,2-diaminocyclohexane platinum(II)

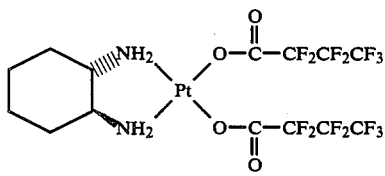

Dichloro(1,2-diaminocyclohexane)platinum(II) (760 mg) and silver nitrate (680 mg) were stirred in the dark at 50° C. for 3 hours. The reaction mixture was chilled for 24 hours and filtered. An excess of sodium heptafluorobutyrate was added to the filtrate and the reaction mixture was heated at 60° C. A precipitate appeared and this was filtered and washed with water to give the title product (350 mg). The product is insoluble in water but soluble in alcohol (ethanol) to 50 mg/ml. In the TLC system n-butanol:acetic acid:H$_2$O (12:3:5) on cellulose, the product gave an $R_f$ of 0.83 (spotting solvent-ethanol with heptafluorobutyric acid). The IR was consistent for the indicated structure.

EXAMPLE 4

Preparation of bis(acetoacetato) trans(−)-1,2-diaminocyclohexane platinum(II)

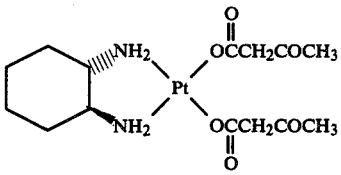

A mixture of cis-dihydroxy-1,2-diaminocyclohexane platinum(II) (343 mg) and acetoacetic acid (220 mg) was heated at 50° C. with stirring for 2 hours. The color of the solution went from yellow to colorless. The title product was isolated from solution by vacuum evaporation and washed with cold alcohol. The product is water-soluble and gave the following $R_f$ values when tested in the indicated TLC systems:

| | |
|---|---|
| n-butanol:acetic acid:water (12:3:5) | 0.88 |
| isopropanol: 0.1N NH4OH (1:1) | 0.83 |

The IR was consistent for the indicated structure.

EXAMPLE 5

Preparation of bis(2-ketobutyrato)trans(−)-1,2-diaminocyclohexane platinum(II)

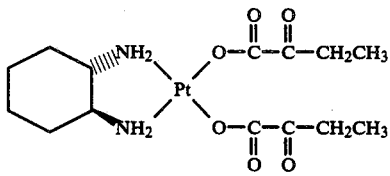

A mixture of cis-dihydroxy-1,2-diaminocyclohexane platinum(II) (343 mg) and ketobutyric acid (224 mg) was heated in water at 50° C. for 1 hour. The solution was then evaporated to dryness and the resulting solid washed with cold alcohol. The title product was obtained as a white solid (315 mg) which is water-soluble but only slightly soluble in alcohol. The product gave the following $R_f$ values when tested in the indicated TLC systems:

| | |
|---|---|
| n-butanol:acetic acid:water (12:3:5) | 0.69 |
| isopropanol: 0.1N NH4OH (1:1) | 0.77 |

The IR was consistent for the indicated structure.

EXAMPLE 6

Preparation of thymidylato trans(−)-1,2-diaminocyclohexane platinum(II)

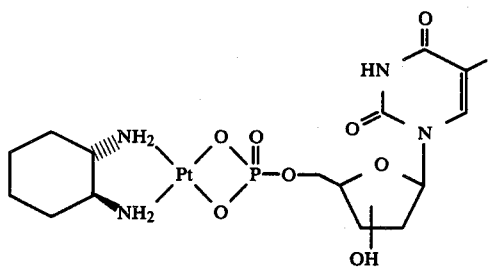

A mixture of dichloro(1,2-diaminocyclohexane) platinum(II) (760 mg) and 1.08 g of disilver thymidine monophosphate was suspended in 30 ml. of water. The reaction mixture was stirred in the dark at room temperature for 36 hours and then evaporated to dryness. The title product obtained (698 mg) was a white material that is water-soluble but alcohol-insoluble. When tested in the TLC systems indicated below, the following $R_f$ values were obtained:

| | |
|---|---|
| n-butanol:acetic acid:water (12:3:5) | 0.55 |
| isopropanol: 0.1N NH4OH (1:1) | 0.89 |

The IR was consistent for the indicated structure.

EXAMPLE 7

Preparation of n-butylboronato trans(−)-1,2-diaminocyclohexane platinum(II)

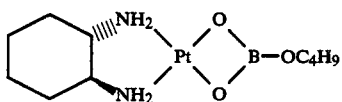

Cis-dihydroxy-1,2-diaminocyclohexane platinum(II) (686 mg) and butylboronic acid (203 mg) were dissolved in water. After heating the reaction mixture at 50° C. for 2 hours, the mixture was evaporated to dryness under vacuum. As the solution was evaporated, a solid material came out of solution. This solid material was collected by filtration and washed with water to give the title product. The product is insoluble in water but quite soluble in alcohol. In the TLC system n-butanol:acetic acid:water (12:3:5) on cellulose, the product gave an $R_f$ of 0.77. The IR was consistent for the indicated structure.

EXAMPLE 8

Preparation of manganato trans(−)-1,2-diaminocyclohexane platinum(II)

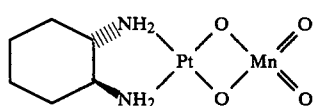

A mixture of dichloro(1,2-diaminocyclohexane) platinum(II) (380 mg) and 305 mg of silver manganate was slurried in the dark for 60 hours. The resulting solution was filtered and evaporated to dryness to give 47 mg of the title product. When tested in the TLC systems indicated below, the following $R_f$ values were obtained:

| n-butanol:acetic acid:water (12:3:5) | 0.74 |
| isopropanol: 0.1N NH4OH (1:1) | 0.35 |

The IR was consistent for the indicated structure.

EXAMPLE 9

Preparation of chromato trans(−)-1,2-diaminocyclohexane platinum(II)

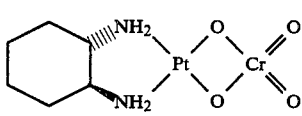

A mixture of dichloro(1,2-diaminocyclohexane)-platinum(II) (380 mg) and 310 mg Ag2CrO4 was suspended in water and stirred for 48 hours in the dark at room temperature. After 48 hours, the solution was filtered and evaporated to dryness to give the title product as a light greenish-yellow solid. The product is soluble in water but only slightly soluble in alcohol. The product was washed with alcohol and dried in vacuo to give a final yield of 85 mg. TLC indicates one band at $R_f=0.74$ in the n-butanol:acetic acid:water (12:3:5) system. The IR was consistent for the indicated structure.

EXAMPLE 10

Preparation of borato 1,2-ddiamino-2,4-dimethylpentane platinum(II)

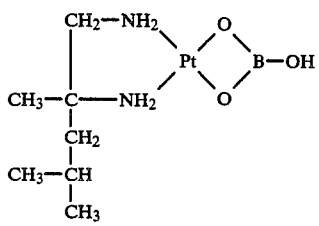

A mixture of cis-dichloro-1,2-diamino-2,4-dimethylpentane platinum(II) (1.179 g) and 936 mg of Ag2SO4 was suspended in 35 ml of water and stirred in the dark at room temperature for 24 hours. The resulting solution was filtered and the filtrate tested for the absence of silver ions. The absence of silver ion indicated the reaction was complete and that sulfato 1,2-diamino-2,4-dimethylpentane platinum(II) had been obtained. There was then added to the filtrate 945 mg of Ba(OH)2 8H2O and the reaction mixture was stirred for 24 hours (a test for Ba ions was negative at this point). The dihydroxy 1,2-diamino-2,4-dimethylpentane platinum(II) product was not isolated. Boric acid (183 mg) was added to the reaction solution and the solution was heated for 1 hour at 50° C. The solution changed from a pale yellow to a dark gold color. The solution was evaporated to dryness to give 0.810 g of title product as a gold solid. The product was water- and methanol-soluble. When tested in the TLC systems indicated below, the following $R_f$ values were obtained:

| n-butanol:acetic acid:water (12:3:5) | 0.68 |
| isopropanol: 0.1N NH4OH (1:1) | 0.95 |

The IR was consistent for the indicated structure.

EXAMPLE 11

Preparation of phosphonoacetato trans(−)-1,2-diaminocyclohexane platinum(II)

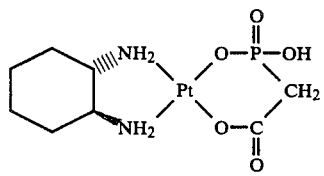

A mixture of cis-dihydroxy-1,2-diaminocyclohexane platinum(II) (646 mg) and phosphonoacetic acid (280 mg) in 15 ml of water was heated at 50° C. for 1 hour. The reaction mixture was evaporated to dryness and washed with ethanol to remove any unreacted starting materials. The product obtained (510 mg) is water-soluble but alcohol-insoluble. IR indicates that phosphonoacetic acted as a bidentate ligand. When tested in the TLC systems indicated below, the following $R_f$ values were obtained:

| n-butanol:acetic acid:water (12:3:5) | 0.35 |
| isopropanol: 0.01N NH4OH (1:1) | 0.15 |

EXAMPLE 12

Preparation of hydroxymethylphosphonato trans(−)-1,2-diaminocyclohexane platinum(II)

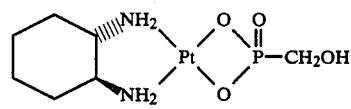

A mixture of cis-dihydroxy-1,2-diaminocyclohexane platinum(II) (686 mg) and hydroxymethylphosphonic acid (224 mg) in 15 ml of water was heated for 1 hour at 50° C. The resulting solution was evaporated to dryness to give title product. The product is soluble in both water and methanol. The product was dissolved in water and precipitated with acetone to remove unreacted starting materials. Yield: 358 mg. When tested in the TLC systems indicated below, the following $R_f$ values were obtained:

| n-butanol:acetic acid:water (12:3:5) | 0.50 |
| isopropanol: 0.1N NH4OH (1:1) | 0.50 |

The IR was consistent for the indicated structure.

EXAMPLE 13

Preparation of borato 1-aminomethylcyclooctylamine platinum(II)

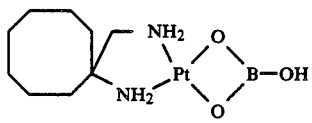

A mixture of cis-dichloro-1-aminomethylcyclooctylamine platinum(II) (844 mg) and 624 mg of Ag$_2$SO$_4$ was suspended in 25 ml water and stirred at room temperature in the dark for 24 hours. The solution was then filtered (no silver was present in the filtrate). There was then added 630 mg Ba(OH)$_2$ 8H$_2$O to the filtrate and the solution was stirred in the dark for 24 hours. The solution was then filtered to remove the BaSO$_4$. Boric acid (126 mg) was added to the filtrate and the solution was heated for 1 hour at 50° C. The solution turned from yellow to gold. Upon evaporation of the reaction mixture to dryness, the title product (455 mg) was obtained. The product is both water- and methanol-soluble. Purification was achieved by dissolution in water and re-precipitation with isopropanol. When tested in the TLC systems indicated below, the following R$_f$ values were obtained:

| n-butanol:acetic acid:water (12:3:5) | 0.65 |
|---|---|
| isopropanol: 0.1N NH$_4$OH (1:1) | 0.90 |

The IR was consistent for the indicated structure.

EXAMPLE 14

Preparation of 2-ketoglutarato trans(−)-1,2-diaminocyclohexane platinum(II)

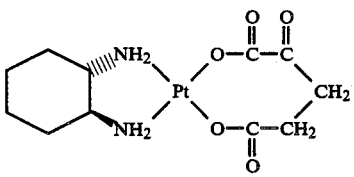

A mixture of cis-dihydroxy-1,2-diaminocyclohexane platinum(II) (686 mg) and 2-ketoglutaric acid (300 mg) was dissolved in 15 ml water, and the reaction mixture was stirred for 2 hours at 50° C. The solution changed color from a bright yellow to light amber. Upon evaporation of the solution to dryness, the title product was obtained as a brown-yellow solid. The product is both alcohol- and water-soluble. When tested in the TLC systems indicated below, the following R$_f$ values were obtained:

| n-butanol:acetic acid:water (12:3:5) | 0.82 |
|---|---|
| isopropanol: 0.1N NH$_4$OH (1:1) | 0.88 |

The IR was consistent for the indicated structure.

EXAMPLE 15

Preparation of phosphonoacetato 1-aminomethylcyclooctylamine platinum(II)

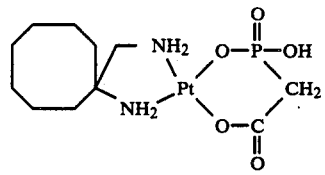

A mixture of cis-dichloro-1-aminomethylcyclooctylamine platinum(II) (1.266 g) and 936 mg Ag$_2$SO$_4$ was suspended in 30 ml water and stirred in the dark at room temperature for 24 hours (the filtrate tested negative for Ag$^+$) Ba(OH)$_2$ 8H$_2$O (945 mg) was added to the filtrate and the resulting solution was stirred in the dark for 24 hours. The solution was filtered to remove BaSO$_4$. The cis-dihydroxy-1-aminomethylcyclooctylamine platinum(II) derivative was not isolated. Phosphonoacetic acid (430 mg) was added to the filtrate and the solution was heated for 1 hour at 50° C. The color of the filtrate changed from yellow to colorless. Upon evaporation of the solution to dryness and washing of the resulting solid with methanol, there was obtained 0.70 g of title product as a light-greenish-white solid. The product is very water-soluble. When tested in the TLC systems indicated below, the following R$_f$ values were obtained:

| n-butanol:acetic acid:water (12:3:5) | 0.41 |
|---|---|
| isopropanol: 0.1N NH$_4$OH (1:1) | 0.21 |

The IR was consistent for the indicated structure.

We claim:

1. A compound of the formula

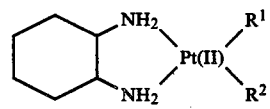

wherein the stereoisomerism of 1,2-diaminocyclohexane is cis-, trans(+) or trans(−) and R$^1$ and R$^2$ when taken together represent a group of the formula

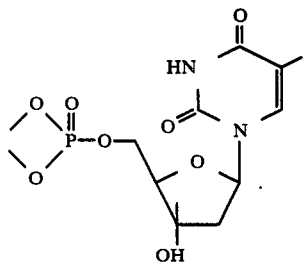

2. A compound of the formula

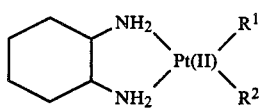
wherein the stereoisomerism of 1,2-diaminocyclohexane is trans(−) and $R^1$ and $R^2$ when taken together represent a group of the formula
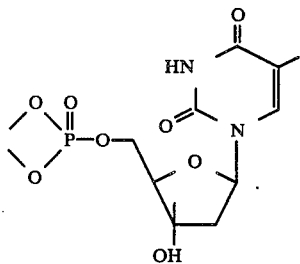
3. The compound having the formula
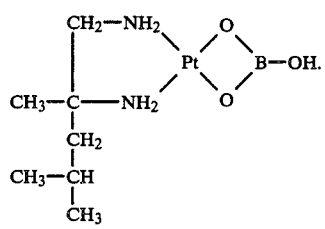
4. A compound having the formula
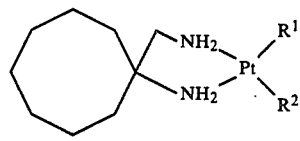
wherein $R^1$ and $R^2$ when taken together represent
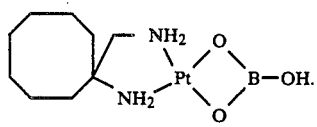
5. The compound of claim 4 having the formula
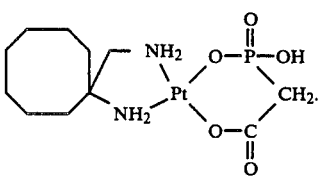
6. The compound of claim 4 having the formula
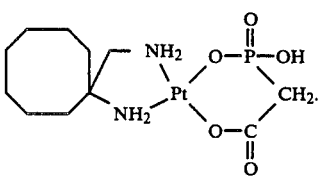
* * * * *